United States Patent [19]
Wilks

[11] Patent Number: 5,432,098
[45] Date of Patent: Jul. 11, 1995

[54] APPARATUS, AND PROCESS, FOR AUTOMATICALLY SAMPLING SOLIDS AND SEMI-SOLIDS MATERIALS FOR ANALYSIS

[75] Inventor: Terry S. Wilks, Greenwell Springs, La.

[73] Assignee: Dynatech Precision Sampling Corporation, Baton Rouge, La.

[21] Appl. No.: 328,791

[22] Filed: Oct. 31, 1994

[51] Int. Cl.⁶ .............................................. G01N 1/10
[52] U.S. Cl. .................................. 436/178; 436/807; 422/99; 422/101; 73/863.81; 73/864.01; 73/864.21; 73/864.81; 73/864.91
[58] Field of Search ............................... 422/99–102, 422/68.1, 81; 436/174, 177–178, 807; 73/863.81, 864.01, 864.21, 864.11, 864.81, 864.91

[56] References Cited
U.S. PATENT DOCUMENTS

| | | | |
|---|---|---|---|
| 3,882,864 | 5/1975 | Montgomery | 128/230 |
| 4,178,660 | 12/1979 | Olney et al. | 17/42.1 |
| 4,553,960 | 11/1985 | Lazarus | 604/158 |
| 4,783,318 | 11/1988 | Lapakko | 422/101 |
| 5,012,845 | 5/1991 | Averette et al. | 141/329 |
| 5,079,170 | 1/1992 | Rosman et al. | 422/100 |
| 5,127,831 | 7/1992 | Bab | 433/80 |
| 5,147,551 | 9/1992 | Averette et al. | 210/640 |
| 5,237,993 | 8/1993 | Skrabal | 128/632 |

*Primary Examiner*—James C. Housel
*Assistant Examiner*—Rachel Freed
*Attorney, Agent, or Firm*—Llewellyn A. Proctor

[57] ABSTRACT

Apparatus, and process, for extracting organic fluids and solids specimens from weighed amounts of semi-solids and solids samples for collection, concentration and transfer to an analytic unit. The organic specimen is picked up by a probe assembly from a single compartment septum-sealed vial by heating and slurrying the sample, contacting with a gas; and then transferring the organic specimen with the gas to a collection device, e.g., a syringe or adsorbent trap. The specimen is then transported to an analytical instrument for analysis.

16 Claims, 4 Drawing Sheets

APPARATUS, AND PROCESS, FOR AUTOMATICALLY SAMPLING SOLIDS AND SEMI-SOLIDS MATERIALS FOR ANALYSIS

FIELD OF THE INVENTION

This invention relates generally to automatic fluid injectors, or instruments of a class used for sampling and analyzing fluid specimens; and more recently, additionally, solids and semi-solids specimens. In particular, it relates to the automatic extraction of soluble organic components, gases, liquids or solids specimens, or gases, liquids and solids specimens, from solids and semi-solids samples for analysis via automated techniques.

BACKGROUND

Automated fluid injection devices, particularly automated needle syringes, have gained wide acceptance by industry and by the scientific and medical communities. This is because these devices are generally capable of dispensing very small, accurately measured quantities of fluid specimens on the order of a few microliters, generally a fractional part of a microliter. In the operation of these devices many samples are prepared in advance, the specimens placed in vials, the vials placed in a magazine, or tray and the samples run with minimal operating labor. Typically, e.g., septum covered bottles, or vials charged with a fluid specimen, are transported in seriatim via a magazine to a station adjacent a probe assembly, a needle of the probe assembly is projected through the septum of a vial and employed as a conduit to convey a portion of the fluid specimen to the barrel of the syringe. The circuit through which the specimen is conducted, and barrel and needle of the syringe are cleaned, purged and a quantity of the fluid specimen is measured out and injected via the needle end of the syringe into the inlet of an analytical instrument, e.g., a G.C. or mass spectrometer. More recently, specimens have been extracted from solids and semi-solids samples and analyzed in much the same way; i.e., the fluid, liquid, or solids specimens are extracted from a solids or semi-solids sample, the specimen then passed to a syringe or an adsorbent or other type of purge trap, and the specimen then displaced from the syringe or trap to the analytical instrument for analysis. The advantages offered by modern data gathering techniques, and consequent reduction in operating man power without loss in accuracy make these devices particularly useful in modern industrial establishments.

Automated apparatus for extracting fluid and solids specimens from solids and semi-solids samples for analysis is disclosed in Averette's U.S. Pat. No. 5,147,551 which issued on Sep. 15, 1992 to Dynatech Precision Sampling Corporation. This instrument departed from earlier models, such as disclosed in Averette's U.S. Pat. No. 5,012,845 which issued on May 07, 1991 to Dynatech Precision Sampling Corporation, which were designed to pick up from vials and process only fluid specimens for analysis. The later instrument, or instrument disclosed in the '551 patent, was adapted to extract for analysis fluid or solid specimens from weighed amounts of solids or semi-solids samples contained within one of the compartments of a compartmented vial. The compartmented vials were carried via a feed tray, or magazine, to a station adjacent to a solids preparation and extraction sub-assembly for processing and pick up of the specimen. Water, or other solvent, was added to the solids or semi-solids material in the upper compartment of the vial, the solids or semi-solids material was crushed and ground, heated, gas was fed into a lower compartment and passed through a frit into the upper compartment to extract the specimen for transport to an automated syringe, or purge trap for containment and subsequent injection into the analytical instrument. However, whereas this instrument has performed admirably, and has extended the field of usage of these instruments, in handling some samples excessive foaming occurs which sometimes interferes with the transfer of the extracted specimen from the compartmented vials. Additionally, inter alia, some simplification may be helpful, and it is desirable to eliminate the need of using compartmented vials for the extraction and analysis.

OBJECTS

It is, accordingly, a primary need to provide such improvements in an automated sampler device for the extraction, or removal of fluid or solids specimen(s) from an organic solid or semi-solids material for collection and transfer to an analytic instrument for analysis.

A further, and more particular object of this invention is to provide apparatus for processing, suitably in automated fashion, weighed solids or semi-solids samples in non compartmented vials, or bottles, delivered in seriatim for the solvent extraction of organic fluid or solids specimen(s) therefrom and for the collection and delivery of the component, or components, taken from these samples to an analytical instrument for analysis.

It is also an object of this invention to provide a process for the extraction, and removal, of an organic fluid or solids specimen from solid or semi-solids materials with accuracy and precision for transfer to a specimen collection device, suitably an automatic fluid injector, or syringe, or to a purge vessel, e.g., an adsorbent trap, for injection or transfer to an analytical instrument.

THE INVENTION

These objects and others are achieved in accordance with the present invention embodying improvements in automatic fluid injectors to render these devices useful in processing for analysis organics, e.g., fluids, gases, or liquids, or solids specimens extracted from solids and semi-solids materials, or both. The instrument is capable of handling, or processing for analysis extremely small fluid specimens per se, and for extracting, or removing, for analysis extremely small organic liquid or solids specimens from solids or semi-solids samples, e.g., paints, plastics, rubber or the like. In a preferred embodiment solids or semi-solids specimens contained in bottles, or vials, are delivered by a feed tray, magazine or carrousel in seriatim, to a solids preparation and extraction station wherein the solids or semi-solids are crushed and ground, contacted directly with a solvent, heated and mixed to dissolve out the organic liquid or solids components from the solid or semi-solids material, the liquid or solids components contacted and vaporized, or otherwise dispersed, in a non-reactive gas, and the non-reactive gas containing the extracted liquid or solids component is then passed to a collection device, suitably a syringe or purge gas trap analyzer, for transfer and subsequent analysis, e.g., in a gas chromatograph or mass spectrometer.

A solids preparation and extraction device is structured to receive, handle and process for analysis the solid or semi-solids containing vials, or bottles, delivered by or picked up from a feed tray, magazine or carrousel. This device is programmable to select the appropriate solid or semi-solids containing vials, or bottles from a feed tray containing other bottles, or vials, which contain only fluids. In its preferred use therefore, the solids preparation and extraction device of this invention is employed as a sub-assembly or (A) a solids preparation and extraction station in combination with other sub-assemblies of an automated fluid injector which includes, or further includes, (B) a syringe, purge gas vessel or adsorbent trap, (C) an injector feed assembly for introducing a fluid specimen into the syringe, or purge vessel, and (D) a feed tray, magazine or carrousel for transporting vials or bottles for pick up of a specimen therefrom by the injector feed assembly for delivery to a specimen concentration device, suitably an adsorbent trap or a syringe as described, e.g., by U.S. Pat. No. 5,012,845, supra. Fluid specimens contained in vials, or bottles, carried by the magazine are programmed to bypass the (A) solids preparation and extraction station, and the specimens are processed in seriatim for delivery to an analytical instrument as fully described at Columns 5–11, and by FIGS. 1–16 of the drawings, herewith incorporated and made a pan of the present application by reference. The vials, or bottles, which contain the solids and semi-solids samples, on the other hand, are serially processed on arrival at the (A) solids preparation and extraction station, on delivery thereto by (D) the feed tray, magazine, or carrousel. The liquid solvent, preheated if desired, is delivered to the vial which contains the solid, or semi-solids from any suitable container, or reservoir, and fed e.g., via a mechanical metering pump. Suitably, e.g., a syringe not in use in processing a solid or semi-solids material can be used for this purpose. The syringe in this instance would thus be used not in its normal capacity as a mechanism for injection of a fluid specimen to an analytical instrument, but to deliver the liquid solvent for contact with the crushed, ground solid or semi-solids component contained in the compartmented bottle for extraction of the fluid or solids component.

The invention, and its principle of operation, will be more fully understood by reference to the following detailed description of a specific and preferred embodiment, and to the attached drawings to which reference is made in the description. Similar numbers are used in the drawing to represent similar pans or components, and subscripts are used with numbers where parts or components are duplicated. Where reference is made in the written text to a component designated by the use of subscripts in the drawing, without reference to the subscripts, the designation is intended in a generic sense.

Reference is made, first generally to the several figures which show a preferred solids preparation and extraction device. This device can be independently mounted in an appropriate housing in the combination subsequently described and employed to process only solid or semi-solids materials delivered on station thereto via a feed tray, magazine or carrousel. Alternatively, this device can be mounted in an appropriate housing with the additional sub-components (B) and (C), supra, to provide an instrument suitable for handling, on the same feed tray, magazine, or carrousel, vials, or bottles, which contain both (i) fluid samples and (ii) solid or semi-solids samples from which organic fluid or solids specimens can be extracted. A full and complete description of an automatic fluid injector for handling fluid containing vials, and its principal of operation, is given in the '845 patent, supra. The '551 patent, supra, on the other hand, contains a description of apparatus for extracting organic fluid and solids specimens from semi-solids and solids samples; and also apparatus for handling both operations employing the same instrument. The present description will focus on a description of the principle of operation and function of a preferred instrument for the extraction of organic fluid and solids specimens from semi-solids or solids samples, and process for carrying out this operation.

Figure 1:
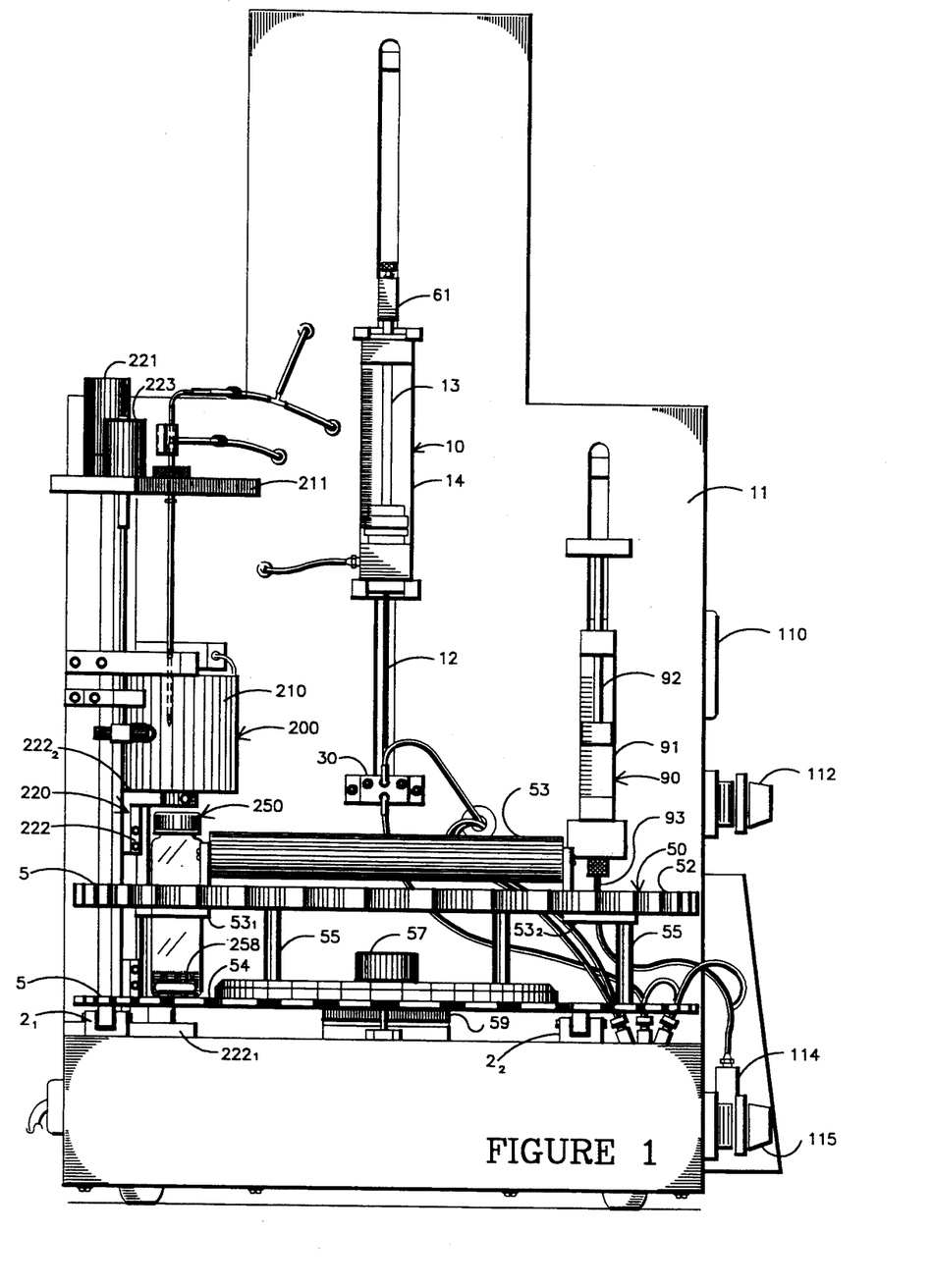
FIG. 1 depicts a left side elevation view of the instrument, this view showing, in particular, the location, position and relationship between the carrousel feed tray at the moment of its having delivered a solids or semi-solids containing septum-sealed vial, or bottle, of a series, to the solids preparation and extraction mechanism at which the vial, or bottles, and others (not shown) are stationed in sequential order on delivery by the carrousel feed tray for crushing and grinding the solid or semi-solids. It also depicts the sample syringe from which, inter alia, a liquid solvent can be supplied for contact with the crushed solids; and as well an adjacent internal standards syringe.

Referring first to FIG. 1, the principle components of the instrument employed to extract and recover the organic liquid or solids components from a given amount of a solid or semi-solids material, and inject said recovered components to an analytical unit, include a solids preparation and extraction sub-assembly 200, a syringe 10, and a carrousel feed tray 50. All are contained within a suitable housing (described by the '845 and '551 patents. The feed tray 50 transports in programmed sequence the bottles 250, containing weighed amounts of the solids or semi-solids samples, to a position for operation thereon by the solids preparation and extraction assembly 200. The carrousel feed tray 50 provides seating locations for the bottles, or vials, in any programmed order as desired for analysis. The circumferential edges of the upper sample tray holder 52 and tray base 54 of the carrousel feed tray 50 within which the bottles or vials are placed are slotted, or cut away providing slots 5 which permit ready access for lifting the vials for processing, and extraction of components for analysis. The details of construction, pick up of the vials from the feed tray 50, and the operation and function of the solids preparation and extraction sub-assembly 250 are hereafter described in detail by reference to FIGS. 1 through 4.

A vial, or bottle 250 useful in the practice of the present invention is best described by reference to FIGS. 2 through 4. Unlike the instrument described by the '551 patent, supra, the apparatus of this invention can utilize a more conventional single compartmented vial, or bottle 250. A weighed solids or semi-solids material is sealed within the vial 250, a solvent is added thereto, the solids or semi-solids material is heated, crushed, ground and stirred to extract the organic liquid or solids specimen, and gas is added to remove the extracted organic liquid or solids specimens from a vial 250 for collection and transport to the inlet of the analytical instrument as subsequently described.

The vial 250 is formed by an enclosing side wall 251, the opening into the upper end of which is sealed by an open-centered, septum-covered end cap 252. Preferably, the upper end of the vial 250 is of reduced diameter and threaded for threadable engagement with, and sealing by the open-centered, septum-covered screw cap 252. Suitably, the small diameter end of the bottle is externally threaded, and the inside opening of the cap 252 is internally threaded for threaded engagement therewith. The central opening within the cap 252 is covered with a septum 254 to provide an impervious gas seal. Various means may be employed to crush and grind the solids or semi-solids sample, but preferably a magnetic stirring device is employed. Thus, preferably a magnetic stirrer device is employed to crush, and grind the solid, or semi-solids sample by rotation of the magnetic stir bar 258 to release the organic liquid or solids component for dispersal or solution within the solvent 257. Gas, e.g., helium injected into the vial via the inner tubular needle $212_1$ of concentric needle assembly 212 will strip out, evaporate and pick up the component dissolved or otherwise removed from the crushed, ground solid and convey the component via the annular passageway of the outer concentric needle $212_2$, and line $212_{2A}$, to, e.g., a syringe, purge vessel or an adsorbent trap (not shown) for collection and subsequent transfer to the analytical instrument (FIG. 4).

Figures 2, 3:
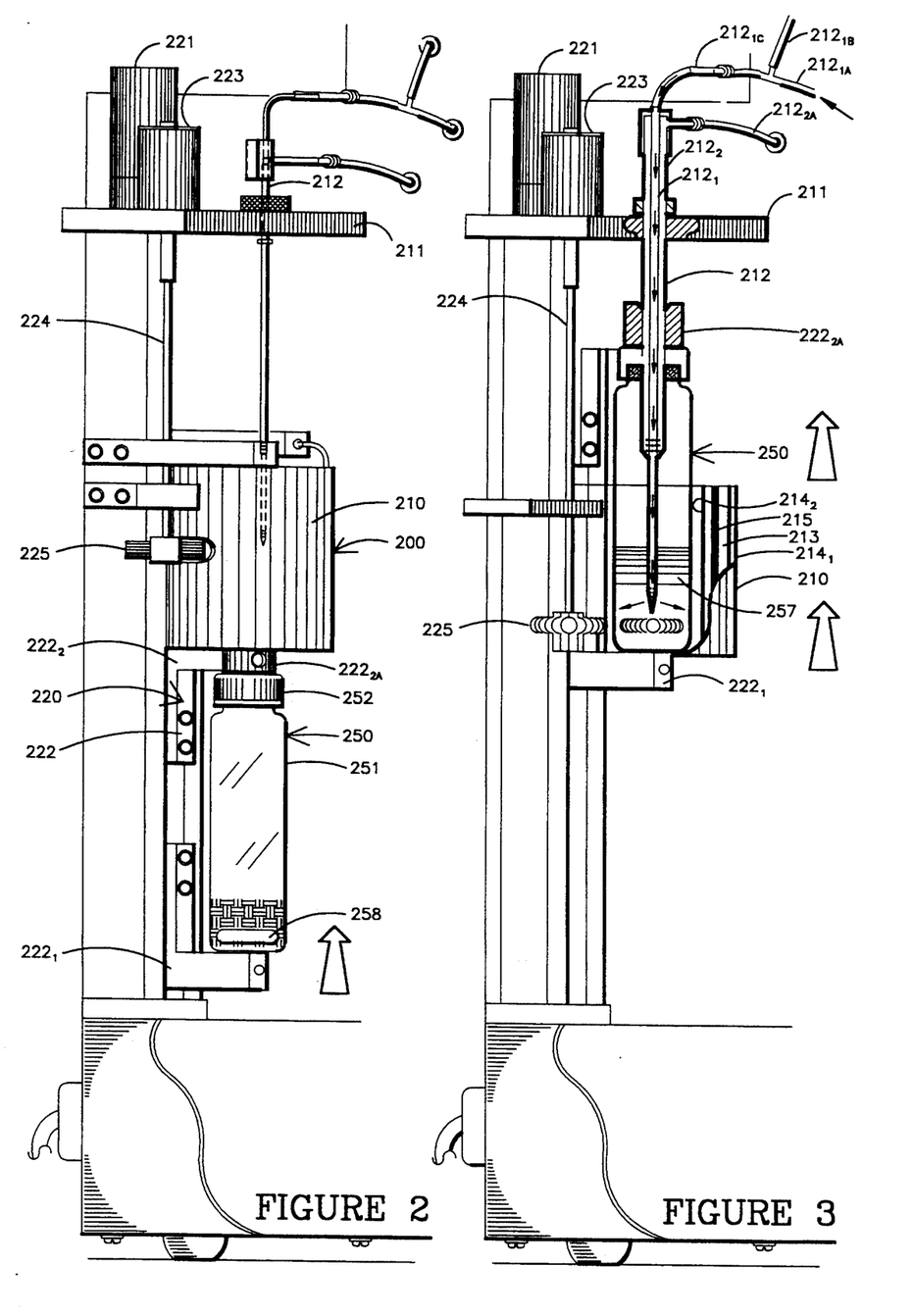
FIG. 2 depicts in some detail a solids or semi-solids containing septum sealed vial, or bottle, and the solids preparation and extraction mechanism.
FIG. 3 depicts the solids preparation and extraction mechanism.
Figure 4:
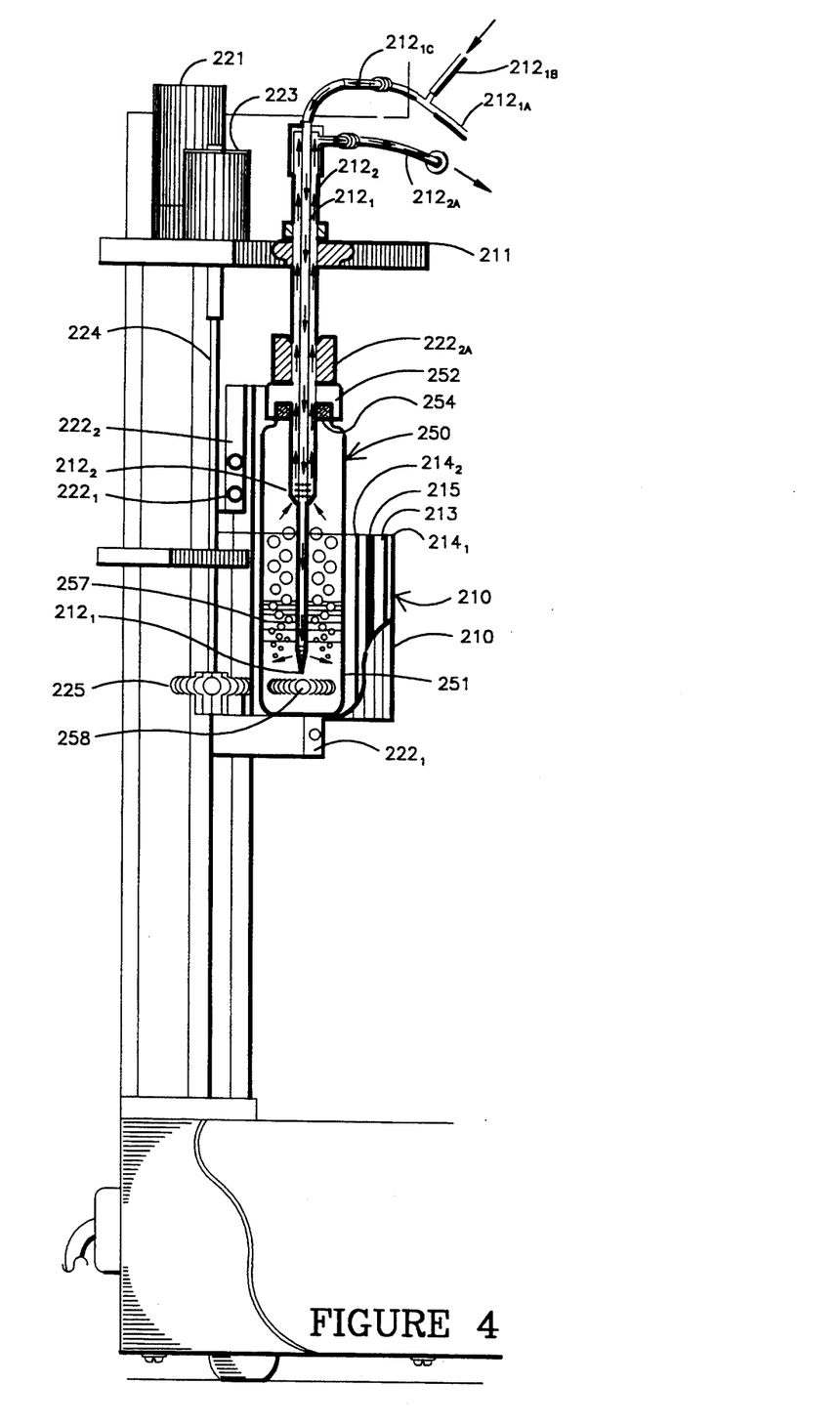
FIG. 4, taken with FIGS. 1–3 describe a cycle of operation beginning with the delivery and positioning of a solids or semi-solid containing septum sealed vial, or bottle, at the solids preparation and extraction station, and continuing through the extraction and injection of an extracted fluid or solid component to e.g., a purge gas trap analyzer.

The solids preparation and extraction sub-assembly 200, as shown by any of FIGS. 1–4, includes generally an electrical heater, or oven 210, and an elevator assembly 220 inclusive of an upper carriage section $222_2$ and a lower carriage section $222_1$. It further includes an elevator motor 221 for raising and lowering the elevator assembly 220, and a stir motor 223 for inductive rotation of the magnetic stir bar 258 contained within vial 250. The electric oven 210, which is secured in place in fixed position upon a generally upright frame structure, housing and tower assembly, below the plate 211, is constituted of an electric heating element-containing wall, to which current is supplied via electrical leads (not shown) surrounding an open space within which the elevator carriage 222, supported upon a generally upright frame structure, housing and tower assembly, and carrying a vial, or bottle 250 within which a solution can be added to contact a solid or semi-solids material, can be raised, housed and heated. The electrical heating element 213, it will be observed, is located between side walls $214_1$, $214_2$ of the heater, and on one side thereof is provided insulation 215. Within the plate 211 is provided an opening or aperture through which the pair of concentrically mounted tubular needles 212 is projected, and rigidly retained in fixed vertical position. The inner needle $212_1$ is connected via a valved line $212_{1A}$ and line $212_{1C}$ (with valved line $212_{1B}$ closed) to a supply source through which a liquid solvent, suitably a preheated liquid solvent if desired, can be introduced (FIG. 3). Alternatively, a gas can be supplied to the inner needle $212_1$ via lines $212_{1B}$, with $212_{1C}$ (with line $212_{1A}$ closed; see FIG. 4). The outer needle $212_2$, with the inner needle $212_1$, provides an annulus through which gas from the headspace above the level of the liquid in bottle 250 can be passed via outlet line $212_{2A}$, (FIG. 4). The elevator assembly 220, constituted of a carriage 222 provided with lower and upper elevator sections $222_1$, $222_2$ are slidably mounted in a vertical groove (not shown) of the housing or tower assembly for upward and downward movement within the support structure, or tower.

The elevator carriage 222 can be reciprocated by the elevator motor 221, the shaft (not shown) of which is geared thereto by a mechanism (not shown). Activation of the stir motor 223 when the carriage 222 is in raised, or elevated position, produces rotation of the magnetic stir bar 258 to crush and grind the weighed solid or semi-solids sample contained in the vial 250, and stir the liquid and solids contents thereof after the solvent, e.g., water, has been added.

A complete cycle of operation, beginning with a reference to FIG. 1 is described as follows: The elevator carriage 222 is shown in its extreme downward position; the vial 250 resting within a slot of the magazine, or carrousel tray 50 where it has been transported by the tray, in a position aligned for pick up by the elevator carriage 222. The vial 250 rests in the carrousel tray 50 at a position below the heater 200.

Referring to FIG. 2, the bottom of the vial 250 is engaged by the lower elevator section $222_1$ of the elevator carriage 222 and lifted, the upper end of the cap 252 now being pressed within the downwardly directed concave face of the bottle guide $222_{2A}$, the bottle 250 being aligned and stabilized as the elevator carriage 222 begins its ascent.

Referring next to FIGS. 3 and 4 it will be observed that the cross-sectional diameters of needles $212_1$, $212_2$ are enlarged to facilitate showing the flow paths of the gases and liquids entering into and leaving the needle assembly 212. Now, continuing the description of a cycle of operation, reference is made to FIG. 3.

The elevator carriage 222, as shown by reference to FIG. 3, continues the ascent and is now lifted to its maximum upward position, being driven to this position by continued activation of the elevator motor 221. As the elevator is lifted the septum 254 of bottle 250 is penetrated by the pointed lower end of inner needle $212_1$ of the concentrically mounted pair of needles 212. On reaching its maximum upward position, liquid solvent, e.g., water, is injected via lines $212_{1A}$, $212_{1C}$ and inner tubular needle $212_1$ into the vial, or bottle 250 to raise the level of the liquid up to but not exceeding a predetermined level. The heating element of heater 210 is now heated, and the stir motor 223 is activated. The magnetic element 225, located on the end of the stir motor shaft 224 is rotated thereby inducing rotation of the magnetic stir bar 258 within the heated liquid. Rotation of the stir bar 258 is continued for a time sufficient to crush and grind the solid or semi-solids material, releasing and extracting the organic fluid or solids components therefrom.

Next referring to FIG. 4, a non-reactive or inert gas, e.g, helium, is input via lines $212_{1B}$, $212_{1C}$ (while line $212_{1A}$ is closed) and needle $212_1$ into the liquid-containing vial 250, the gas exiting from the perforated openings at the terminal end of the needle, bubbling upwardly through the liquid. Suitably, when the liquid solvent is added to the vial, or bottle 250, gas flow is initiated to flow through the solvent-solids mixture simultaneously, with heating and stirring. Rotation of the magnetic stir bar 258 is continued as the gas passes upwardly partially as very fine bubbles, through the stirred slurry of water and finely divided solids. Liquid and solids components, particularly volatile organic contaminants as may be contained in, e.g., a soil sample, are released from the solids or semi-solids materials as the extraction becomes virtually complete. The vapors are removed from the vapor space of the bottle 250 via the annular passageway located between the outside wall face of needle $212_1$, and the inside wall face of needle $212_2$, and passed via line $212_{2A}$ to a sample concentrator, suitably a syringe or adsorbent trap, and then to an analytical instrument. Preferably, the specimen is passed to a packed column, or "trap". Upon completion of the flow through the purge cycle, gas flow through the trap is reversed and, e.g., the volatile organic contaminants held by the trap are carded to an analytical instrument, e.g., a gas chromatograph or mass spectrometer.

The cycle begins anew with return of the elevator carriage 222 to its downward position, and the delivery of a new bottle or vial, by the carrousel feed tray 50 as depicted by reference to FIG. 1.

Figure 5:
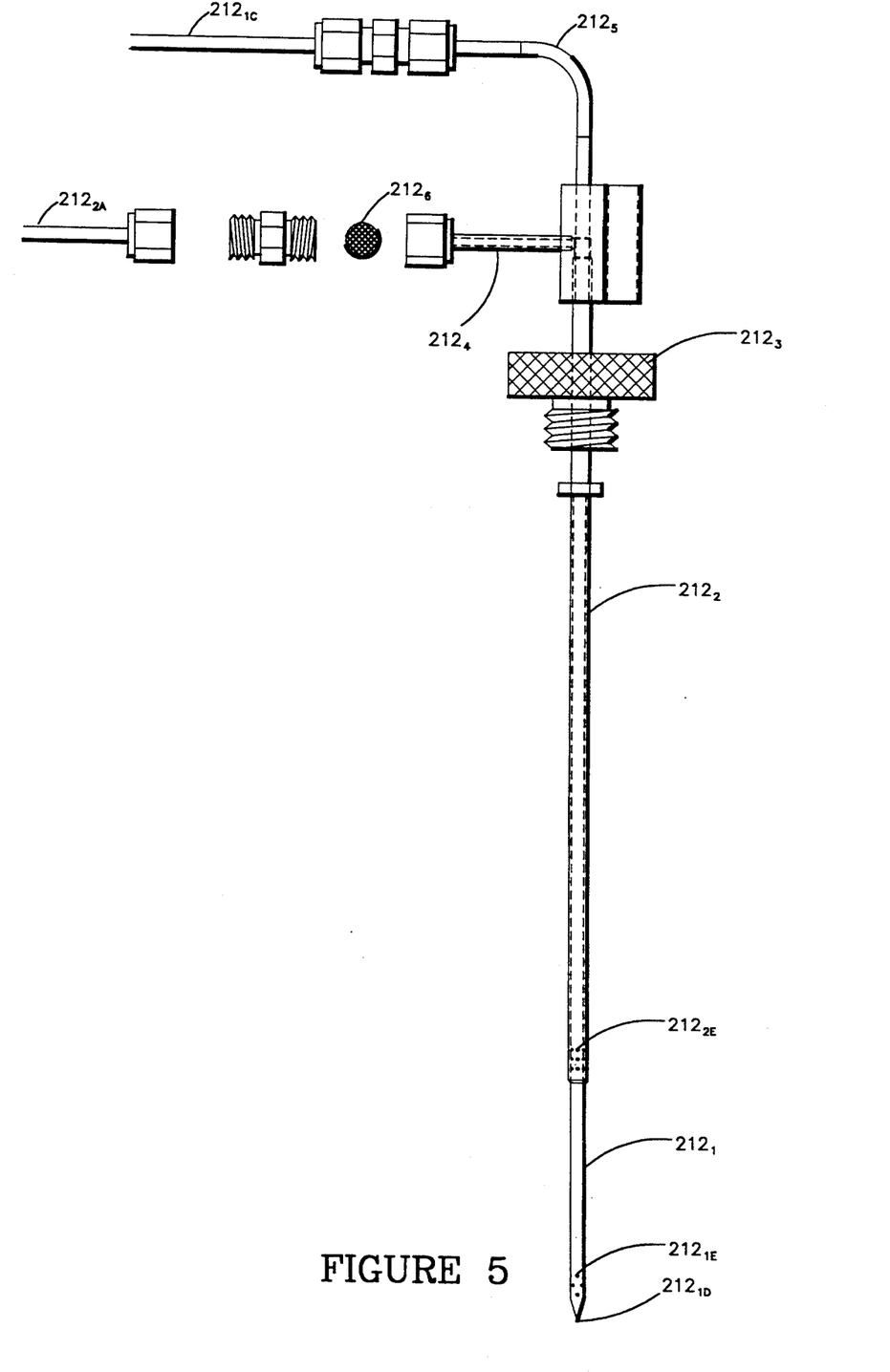
FIG. 5 depicts in somewhat greater detail a preferred probe assembly.

Referring to FIG. 5, a preferred probe assembly is shown in somewhat greater detail; the probe assembly including a pair of concentric tubular needles 212, an inner needle $212_1$, and an outer needle $212_2$. The enclosing wall forming the inner needle $212_1$ is of relatively small external diameter, whereas the wall forming the outer needle $212_2$ is of larger diameter, having an internal diameter sufficient to provide an annulus, or annular passageway between the external wall face of the inner needle $212_1$ and internal wall face of the outer needle $212_2$; the annular passageway being concentrically aligned upon the axis of the bore through the inner tubular needle $212_1$. The lower terminal end of the inner tubular needle $212_1$ tapers to a sharp point $212_{1D}$, a plurality of radially dispersed wall apertures $212_{1E}$ being provided to form a filter opening into the bore of the inner needle $212_1$. A plurality of radially arrayed wall apertures $212_{2E}$ at the terminal lower end of outer needle $212_2$ also provide a filter opening into the annulus, or annular opening between the external wall face of the inner needle $212_1$ and inner wall face of the outer needle $212_2$. The open centered externally threaded bolt $212_3$, with large knurled knob, through which the pair of needles 212 is passed and retained, provides a means for attachment and suspension of the needles 212 within the plate 211 of the housing structure. A pair of tubular metal conduits $212_4$, $212_5$, are silver soldered in place to form passageways which communicate with the annular passageway and bore through the inner tubular needle $212_1$, respectively; and to each of these, respectively, can be connected lines $212_{1A}$ and $212_{1C}$.

The conduits $212_4$, $212_5$ are connected, or coupled, to lines $212_{2A}$, $212_{1C}$, respectively, via union and ferrule connections; the union and ferrule connection between conduit $212_5$ and line $212_{1C}$ being shown in coupled fashion, while the union and ferrule connection between conduit $212_4$ and line $212_{2A}$ is shown in uncoupled position, and includes a screen filter $212_6$ to remove solids particulates which may be transported through the annulus between the two concentric needles $212_1$, $212_2$.

The plurality of holes, or openings $212_{1E}$ circumferentially arrayed, and located near the terminal end, just above the point $212_{1D}$ of inner needle $212_1$, provide filtered access for the transfer of liquid and gas from the inside passageway through the needle to the chamber of the vial. The use of a plurality of openings increases purge efficiency and minimizes the risk of coring, or solids pluggage as the needle is passed through the septum of the vial. The sum total area of the openings, preferably numbering from about 4 to about 8, is approximately equal to or greater, preferably ranging from about 1 to about 2 times the inside diameter of the needle $212_1$, and more preferably is about 1; or approximately the inside diameter of the needle $212_1$.

The number of holes, or openings, $212_{2E}$ at the lower end of needle $212_2$, generally ranges from about 12 to about 24; and are arrayed about the circumference of the needle generally in about 2 to about 4 rows. The sum total area provided by the openings $212_{2E}$ is approximately equal to or greater, preferably approximating from about 1 to about 4 times, more preferably from about 1 to about 2 times, the cross-sectional diameter of the annular passageway lying between the inside face of the enclosing wall which forms outer needle $212_2$ and the outside face of the wall which forms inner needle $212_1$. The openings $212_{2E}$ minimizes or prevents coring of the septum, maximizes the seal around the probe itself, minimizes back pressure, and acts as a filter screen to eliminate plugging and active site formation. The absolute diameter of each of the holes, or openings $212_{2E}$ is generally somewhat smaller than the holes, or openings $212_{1E}$ of needle $212_1$, typically approximating e.g., 1/16 inch in diameter. The filter openings makes feasible back flushing with liquid, e.g., water, through openings $212_{1E}$, $212_{2E}$ to dislodge particles and eliminate particulate solids plugging.

It is apparent that various modifications and changes can be made without departing the spirit and scope of the present invention. The apparatus is constructed of materials substantially inert or non-reactive to the chemical or corrosive action of the solids, semi-solids or fluid components contained within the specimens handled. The bottle, or vials, are normally constructed of a clear plastic, or glass and the caps used therewith of a hard plastic or plastic-like material. The septum, and sealing components of the bottles, or vials, and as well the tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or plastic-like materials, such as natural or synthetic rubbers can also be employed.

The carrousel feed tray, the solids preparation and extraction sub-assembly, the housing and various other components of the instrument is constructed of conventional metals, e.g., ferrous metals such as iron, iron alloys, steel, stainless steels, and the like; or such metals as aluminum, magnesium, brass, copper, bronze, chrome, alloys of these and other metals, and the like.

Having described the invention, what is claimed is:

1. An apparatus useful for the pick up from a septum sealed vial of an organic specimen contained in a slurried liquid phase above which is provided a gas phase, for transport of the specimen to a specimen collector for delivery to an analytical instrument, comprising:

a pair of concentrically mounted needles, wherein a first one of said concentrically mounted needles is an inner tubular needle having a bore therethrough formed by an enclosing wall, a gas outlet at a lower closed terminal end of the needle formed by a plurality of wall apertures providing a filter opening within the bore, and an upper gas inlet communicated with the bore of said inner tubular needle, and the second of said concentrically mounted needles is an outer tubular needle having a bore therethrough formed by an enclosing wall of diameter sufficiently large to encompass said inner tubular needle and provide an annular passageway between the outside wall face of said inner tubular needle and inside wall face of said outer tubular needle, a gas inlet at the lower terminal end of the outer tubular needle terminating above the gas outlet at the lower terminal end of said inner tubular needle, said inlet consisting of a plurality of wall apertures providing a filter opening to the annular passageway, and gas outlet at the upper terminal end of the outer tubular needle communicated with the annular passageway, whereby, when the lower terminal end of the inner tubular needle is passed through a septum and vapor phase into a liquid phase of a vial, with the lower terminal end of the outer tubular needle lying in the vapor phase of the vial contents, gas is passed via the gas inlet of the inner tubular needle into the bore of the inner tubular needle to exit via the filter opening thereof to pressurize the contents of the vial and mix with the slurried liquid, which carries the specimen, thereby forming a gas, which carries the specimen, which enters into the filter opening at the lower end of the outer tubular needle, passing through the annular passageway and exits the gas outlet of the outer tubular needle for transport to a specimen collector for delivery to an analytical instrument.

2. The apparatus of claim 1 wherein the lower terminal end of the inner needle is provided with a pointed tip below the wall apertures to facilitate entry and passage of the needle through the septum of the vial, and the filter openings to the bore provided by the plurality of wall apertures provides an opening of total area ranging from about 1 to about 2 times the inside diameter of said inner needle.

3. The apparatus of claim 1 further comprises, a septum sealed vial, and means are provided therein for crushing and grinding a weighed solids or semi-solids sample added to the liquid portion of the vial to extract a liquid dispersable specimen therefrom for transport to a specimen collector, and delivery to an analytical instrument.

4. The apparatus of claim 3 wherein the solids or semi-solids sample crushing and grinding means for extraction of the specimen is a stir bar located within the liquid contents of the vial, and the stir bar is driven by a magnetic motor.

5. An apparatus useful for the pick up from a septum sealed vial of a specimen contained in a slurried liquid phase above which is provided a gas phase, for transport of the specimen to a specimen collector for delivery to an analytical instrument, comprising in combination:

a vial sealed with a septum, a specimen collector within which a specimen is contained, and concentrated, a probe assembly, having a pair of concentrically mounted needles, wherein a first one of said concentrically mounted needles is an inner tubular needle having a bore therethrough formed by an enclosing wall, a gas outlet at a lower closed terminal end of the needle formed by a plurality of wall apertures providing a filter opening within the bore, and an upper gas inlet communicated with the bore of said inner tubular needle, and the second of said concentrically mounted needles is an outer tubular needle having a bore therethrough formed by an enclosing wall of diameter sufficiently large to encompass said inner tubular needle and provide an annular passageway between the outside wall face of said inner tubular needle and the inside wall face of said encompassing outer tubular needle, a gas inlet at the lower terminal end of the outer tubular needle terminating above the gas outlet at the lower terminal end of said inner tubular needle, said inlet consisting of a plurality of wall apertures providing a filter opening to the annular passageway, and gas outlet at the upper terminal end of the outer tubular needle in communication with the annular passageway, a line from a gas supply source connected to the gas inlet of said inner tubular needle through which a gas is passed into the bore thereof to exit via the gas outlet at the lower terminal end of the inner tubular needle into the vial for pressurizing the contents of said vial, and mix with a slurried liquid within the vial, which carries a specimen, a line connected to the outlet of the upper end of said outer tubular needle through which the specimen-containing gas is transported to the specimen collector for delivery to an analytical instrument after the lower terminal end of the inner tubular needle has been passed through the septum of the vial and vapor phase into the liquid phase of the vial.

6. The apparatus of claim 5 wherein the lower terminal end of the inner needle is provided with a pointed tip below the wall apertures to facilitate entry and passage of the needle through the septum of the vial.

7. The apparatus of claim 5 wherein means are provided in the vial for crushing and grinding a weighed solids or semi-solids sample added to the liquid portion of the vial to extract a liquid dispersable specimen therefrom for transport to a specimen collector, and delivery to an analytical instrument.

8. The apparatus of claim 7 wherein the solids or semi-solids sample crushing and grinding means for extraction of the specimen is a stir bar located within the liquid contents of the vial, and the stir bar is driven by a magnetic motor.

9. The apparatus of claim 5 wherein a pair of lines, alternately operable, are connected with the outlet from the inner tubular needle, one line providing during part of an operating cycle a means for delivery of liquid from a liquid supply source to the vial to clean the filter opening at the lower terminal end of the needle, and at another part of an operating cycle a liquid solvent for slurrying the solids or semi-solids organic specimen-containing material.

10. In a process for the extraction and separation for analysis of an organic fluid or solids specimen from a semi-solids or solids sample carried within a septum sealed vial having a single compartment the combination of steps which comprise projecting a probe assembly through said septum into the compartment of the vial, said probe assembly including a pair of concentrically mounted needles, wherein a first one of said concentrically mounted needles is an inner tubular needle having a bore therethrough formed by an enclosing wall, a gas outlet at a lower closed terminal end of the needle formed by a plurality of wall apertures providing a filter opening into the bore, and an upper gas inlet communicated with the bore of said inner tubular needle, and the second of said concentrically mounted needles is an outer tubular needle having a bore therethrough formed by an enclosing wall of diameter sufficiently large to encompass said inner tubular needle and provide an annular passageway between the outside wall face of said inner tubular needle and the inside wall face of said outer tubular needle, a gas inlet at the lower terminal end of the outer tubular needle terminating above the gas outlet at the lower terminal end of said inner tubular needle, said inlet consisting of a plurality of wall apertures providing a filter opening to the annular passageway, and gas outlet at the upper terminal end of the outer tubular needle in communication with the annular passageway, a first line from a gas supply source connected to the gas inlet of said inner tubular needle through which a gas is passed into the bore thereof to exit via the gas outlet at the lower terminal end of the inner tubular needle to pressurize the contents of the vial, a second line connected to the gas outlet at the upper end of said outer tubular needle through which a specimen-containing gas is transported, injecting a liquid solvent via said first line into the bore of said inner tubular needle, the liquid solvent exiting at the opening at the lower terminal end of the inner tubular needle to fill the vial compartment to a predetermined liquid level, heating, crushing, and grinding the semi-solids or solids sample within the liquid solvent to form a slurry, injecting a gas via said first line into the bore of said inner tubular needle, the gas exiting from the lower terminal end of said inner tubular needle, pressurizing the contents of the vial and mixing with the liquid slurry, and passing gas into the annular passageway of the outer tubular needle, the gas exiting from the second line to a specimen collector for concentration therein, and transfer therefrom for analysis in an analytical instrument.

11. The process of claim 10 wherein the terminal lower end of the inner tubular needle of the probe assembly terminates as a point to facilitate passage through the septum of the vial, and wherein the point includes the plurality of wall apertures.

12. The process of claim 11 wherein the wall apertures forming the filter provides an opening of total area ranging from about 1 to about 2 times the inside diameter of said inner needle.

13. The process of claim 10 wherein the lower terminal end of the outer tubular member includes a plurality of wall apertures which forms a filter.

14. The process of claim 13 wherein the wall apertures forming the filter provides an opening of total area ranging from about 1 to about 4 times the cross-sectional diameter of the annular passageway formed between the two needles.

15. The process of claim 10 wherein the terminal lower end of the inner tubular needle of the probe assembly terminates as a point to facilitate passage through the septum of the vial, and terminal lower ends of both needles of the probe assembly includes a plurality of wall apertures which form filters.

16. The process of claim 10 wherein the second line connected to the outlet of said inner needle of the probe assembly is valved, and a valved third line is adjoined to said second line forward of the valve portion of the second line, these providing a pair of channels connected to the outlet of said inner needle for the input of liquid solvent to the vial and removal of the specimen containing liquid solvent from the vial via the other, respectively.

* * * * *